(12) United States Patent
Sander et al.

(10) Patent No.: US 8,221,776 B1
(45) Date of Patent: Jul. 17, 2012

(54) PHOSPHOROAMIDOTHIOATE GRANULES AND METHODS OF MANUFACTURE THEREOF

(76) Inventors: William A. Sander, Arlington, TN (US); Paul C. Manning, Lakeland, TN (US)

( * ) Notice: Subject to any disclaimer, the term of this patent is extended or adjusted under 35 U.S.C. 154(b) by 1160 days.

(21) Appl. No.: 11/786,222

(22) Filed: Apr. 11, 2007

Related U.S. Application Data

(60) Provisional application No. 60/801,775, filed on May 19, 2006.

(51) Int. Cl.
*A01N 25/12* (2006.01)
*A01N 57/28* (2006.01)

(52) U.S. Cl. .......................... 424/409; 424/405; 514/120

(58) Field of Classification Search .................. None
See application file for complete search history.

(56) References Cited

U.S. PATENT DOCUMENTS

| | | |
|---|---|---|
| 3,716,600 A | 2/1973 | Magee |
| 3,845,172 A | 10/1974 | Magee |
| 3,914,417 A | 10/1975 | Magee |
| 5,075,058 A | 12/1991 | Chan et al. |
| 5,100,667 A | 3/1992 | Chan et al. |
| 5,298,501 A | 3/1994 | Cummings |
| 5,352,674 A | 10/1994 | Cummings |
| 5,369,100 A | 11/1994 | Cummings |
| 5,464,623 A | 11/1995 | Chan et al. |
| 6,013,272 A | 1/2000 | Cummings et al. |
| 6,337,323 B2 | 1/2002 | Cummings et al. |
| 6,752,943 B1 | 6/2004 | Jadhav et al. |
| 6,761,897 B2 | 7/2004 | Cummings et al. |
| 6,875,381 B2 | 4/2005 | Jadhav et al. |
| 2005/0048094 A1* | 3/2005 | Jadhav et al. ................. 424/405 |

FOREIGN PATENT DOCUMENTS

WO 98/26656 A1 5/2001

OTHER PUBLICATIONS

Hosokawa Micron BV, "The Art of Agglomeration", Believed to be Prior to May 19, 2006, 6 Pages.
bepek corporation, A subsidiary of Berwind Corporation, "K-G/Schugi Unique Vertical Continuous Blender-Agglomerator", Prior to May 19, 2006, 8 Pages.

* cited by examiner

*Primary Examiner* — Neil Levy
(74) *Attorney, Agent, or Firm* — Pearne & Gordon LLP

(57) ABSTRACT

A method of producing a granule containing at least 40 weight percent phosphoroamidothioate, preferably acephate, by processing the phosphoroamidothioate in powder form along with a liquid through a vertical continuous noncompressive agglomerator having a vertical rotating shaft on which are mounted a plurality of adjustable blades.

20 Claims, 1 Drawing Sheet

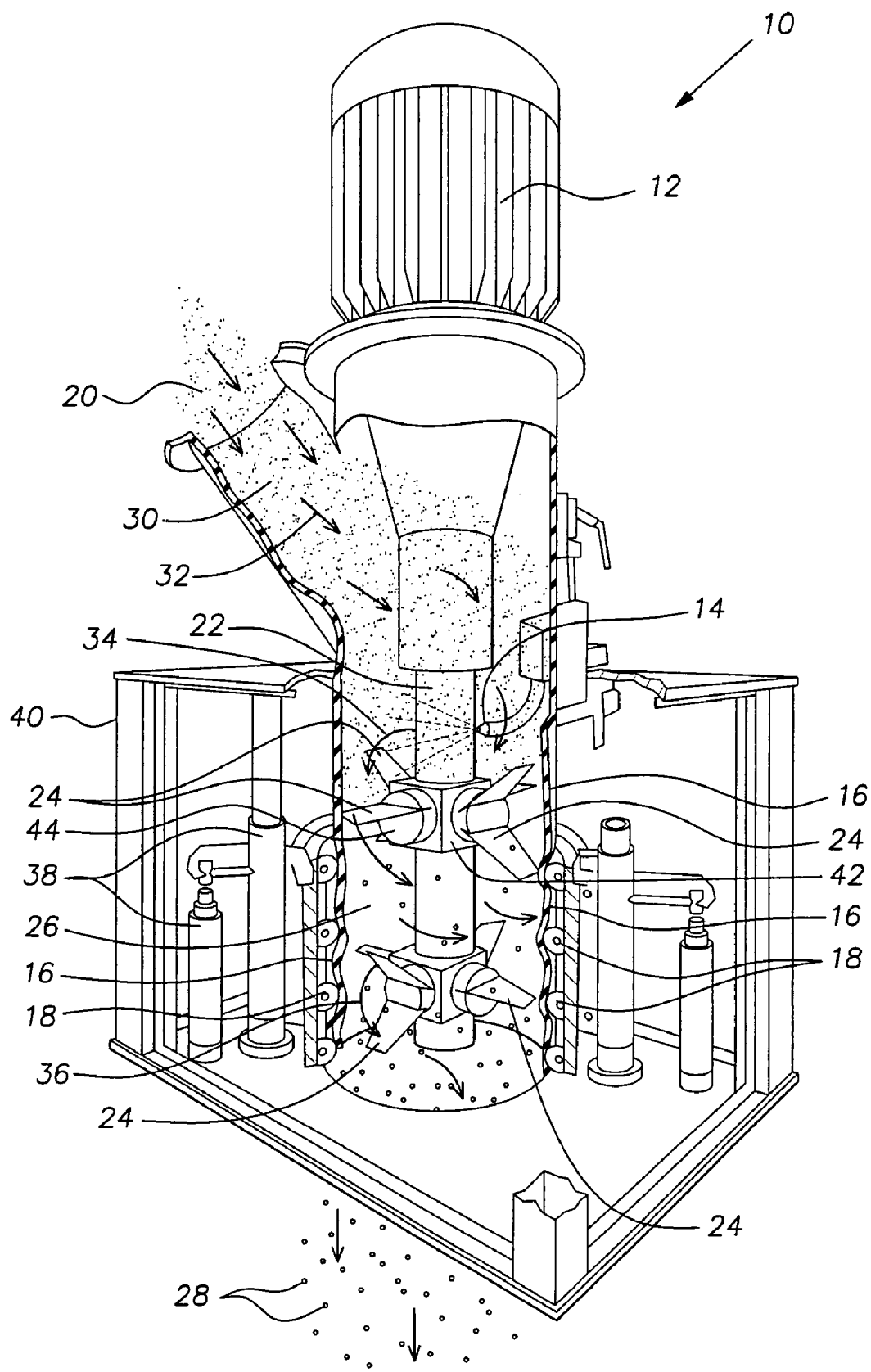

PHOSPHOROAMIDOTHIOATE GRANULES AND METHODS OF MANUFACTURE THEREOF

CROSS-REFERENCE TO RELATED APPLICATIONS

This application claims the benefit of U.S. Provisional Patent App. Ser. No. 60/801,775 filed May 19, 2006, the entire contents of which are incorporated herein by reference.

FIELD OF THE INVENTION

The invention relates to insecticidally active phosphoroamidothioate granules and methods of manufacture thereof.

BACKGROUND OF THE INVENTION

As used hereinafter and in the claims, phosphoroamidothioate means phosphoroamidothioate and phosphoroamidodithioate. Certain phosphoroamidothioates are known in the art as having excellent insecticidal activity against a variety of insects. A particularly important commercial insecticide within this class of compounds is the insecticide acephate (generic name) or Orthene® (trade name), which can be systemically taken up by a plant so that insects which feed and/or live on the plant are killed, in addition to those insects which directly ingest or are contacted by the insecticide. Acephate and related compounds are described in U.S. Pat. Nos. 3,716,600, 3,845,172 and 3,914,417, which disclose that in addition to their insecticidal properties, the compounds possess very low mammalian toxicity. Orthene is commercially produced as a technical grade chemical of about 97 to 99.5% purity (typically about 98%), which is often referred to as acephate technical or acephate TG (technical grade).

Acephate technical is commercially available as a powder, which has a tendency to clump or agglomerate. In the past, acephate technical has been applied to crops as a dust (for example, after exposure to moisture via rain, dew or irrigation), or in spray form as a water solution spray. Dusts are undesirable because of airborne contamination and handling difficulties, while liquid spray formulations involve solvent and packaging expenses, and container disposal requirements that detract from commercial desirability.

In recent years, suggestions have been made to provide phosphoroamidothioates in a pellet form or other type of granule. Phosphoroamidothioate-containing pellets and granules have been proposed in U.S. Pat. Nos. 5,075,058, 5,100,667, 5,464,623, 5,298,501, 5,352,674, 5,369,100, 6,013,272, 6,337,323, 6,761,897, 6,875,381, and 6,752,943; the entire contents and disclosures of each of these patents is hereby incorporated herein by reference. Pellets and other granules have the advantages of eliminating dust problems and reducing offensive odors in comparison to powder forms because of a reduced surface area to weight ratio. However, there is a need for an improved process to produce improved granules, the improved process being more productive with less cost to produce improved granules.

SUMMARY OF THE INVENTION

A method of producing a granule containing phosphoroamidothioate comprising the steps of providing phosphoroamidothioate in powder form along with a liquid to a noncompressive agglomerator and processing said powder and said liquid through said agglomerator to yield a granule which is, on a dry basis, at least 40 weight percent phosphoroamidothioate. A granule produced by the method is also provided.

BRIEF DESCRIPTION OF THE DRAWINGS

FIG. 1 is a perspective, cut-away view of a vertical continuous noncompressive agglomerator useful in the present invention.

DETAILED DESCRIPTION OF THE PREFERRED EMBODIMENTS OF THE INVENTION

As used herein, when a range, such as 5 to 25 (or 5-25) is given, this means preferably at least 5 and, separately and independently, preferably not more than 25. Unless otherwise indicated or apparent, percents are weight percents. Unless otherwise indicated, meshes and screen sizes are U.S. Standard size.

With reference to FIG. 1 there is shown a continuous, in-line vertical gravity flow noncompressive agglomerator 10 useful in the present invention. Agglomerator 10 includes housing 40 and an electric motor 12 which spins (in a counterclockwise direction when viewed from the top) a central vertical free hanging rotating shaft 22 on which are mounted two bladeholders 42 on each one of which are mounted a plurality of adjustable blades 24; each blade 24 being adjustable through 360° by rotating its circular baseholder 44. Preferably the shaft 22 is fitted with 2 or 3 bladeholders 42 with preferably 6 blades on each holder arranged symmetrically as shown. The shaft 22 has a long bearing support clear of the product stream. In operation, fines or powders 20 (which can comprise one or more different powders) are provided to the agglomerator 10 through an inlet channel 30 as shown via arrows 32. As the powders 20 are fed through the top of the agglomerator 10 and pass through by gravity in a continuous stream, liquids are injected via spray nozzles on liquid injectors 14 placed around the top of the vertical cylindrical mixing chamber 26. 1, 2, 3, 4, or more liquid injectors 14 to inject one or more liquids of the same or different viscosities can be placed evenly and concentrically around the top or upper portion of the cylindrical mixing chamber 26. The liquid spray is generally atomized using compressed air. The powder 20 and liquid spray are turbulently mixed in chamber 26 (which is preferably 160-400, such as 160, 250, 335 or 400, mm in diameter) by the rapidly spinning or rotating adjustable blades 24 and spiral downward as shown by arrows 34, 36. Discrete agglomerated granules 28 drop out the bottom of the unit. The short retention time in chamber 26 (less than 2 seconds or less than 1 second) make high production rates possible. Control over particle size, density, and dispersibility can be accomplished by adjusting rotor speed (1000-3500 RPM), rotor element (blade angle) pitch, feed rate, and binder/solid ratio. As can be seen, the agglomerator 10 operates in a continuous, non-batch manner and agglomerates in a noncompressive manner, that is, it does not use compressive force to compress or extrude the powder material into granules or pellets. An extruder operates in a compressive manner and uses compressive force to extrude the material into pellets.

Agglomerator 10 preferably has a continuously deforming mixing chamber 26 which is surrounded by a cylindrical flexible neoprene or elastomeric sidewall 16 which is continuously deformed and massaged by a plurality of pneumatically operated sidewall rollers 18 which are moved vertically along the outside of the sidewall 16 via pneumatic translation apparatus 38. This helps avoid material buildup by keeping wetted particles from adhering to the chamber wall although a slight layer of product remains on the inner wall preventing excessive wear of the neoprene. In addition to reducing clogging, this action helps inhibit particulate over-densification while yielding a more uniform particle with more consistent density, cohesiveness and solubility. Alternatively and less preferably agglomerator 10 can be provided with a rigid metal sidewall 16 and without sidewall rollers 18.

Agglomerator 10 is preferably K-G/Schugi Blender-Agglomerator Flex-O-Mix, such as Model Nos. 160, 250, 335, or 400, manufactured by Schugi B.V., Amsterdam, The Netherlands and distributed by K-G Division of Bepex Corporation, Rosemont, Ill., less preferably the corresponding Schugimix machine (with rigid sidewall) from the same manufacturer and distributor; the foregoing machines are noncompressive agglomerators. These machines are known in the agglomerator art.

Preferred formulations for the invented granules, on a dry basis, are as follows.

| INGREDIENTS (by weight percent) | | | |
|---|---|---|---|
| | Preferred wt. % | More preferred wt. % | More preferred wt. % |
| Phosphoroamidothioate, preferably acephate or acephate TG | 40-100 | 90-99 | 94-95 |
| | 60-100 | 91-98 | 95-99 |
| | 80-100 | 92-97 | 96-99 |
| | 85-100 | 93-96 | 97-99 |
| Filler or Inert Filler | 0-60 | 0-15 | 4-7 |
| | 0-40 | 1-10 | 5-6 |
| | 0-20 | 2-9 | |
| | | 3-8 | |
| Binding Agent | 0-10 | 2-8 | 5-6 |
| | 0.1-5 | 2-9 | 6-7 |
| | 1-9 | 3-8 | 7-8 |
| | 1-3 | 4-7 | |

The phosphoroamidothioate used is preferably acephate, which is available as acephate TG. Acephate TG is commercially available and is about 98 wt. % pure. The filler or inert filler is preferably zeolite or clay or other fillers known in the art, preferably water dispersible, which are preferably added as dry powders. The binding agent is optional and is added to make the granules stronger and harder.

If a binding agent is desired, the filler can be reduced by the amount of binding agent added. The binding agent can be starch or Agrimer or potassium sulfate or other binding agents known in the art; Agrimer (polyvinylpyrrolidone) can be Agrimer VA6 (vinyl pyrrolidone/vinyl acetate copolymer) or similar. Starch and Agrimer are preferably added as dry powders; potassium sulfate is preferably added as part of the water. The weight percent of (a) filler and (b) binding agent in the dry formulation can be 0 or can be preferably at least, or not more than, 1, 2, 3, 4, 5, 6, 7, 8, 9, 10, 11, 12, 13, 14, or 15, weight percent. The fillers and binding agents can be soluble or non soluble in water. A preferred formulation which is about 90 wt. % acephate is about 92 wt. % acephate TG, 6 wt. % zeolite or other filler, and 2 wt. % starch or other binding agent (alternatively, the starch or binding agent can be 0-4 wt. % and the zeolite can be 4-8 wt. %, with the acephate TG remaining at about 92 wt. %). Another preferred formulation is 98.5 wt. % acephate TG and 1.5 wt. % binder such as starch, potassium sulfate, Agrimer or other binding agent. Another preferred formulation is 100% acephate TG, which has a natural clumping ability. Another preferred formulation which is about 75 wt. % acephate is about 76.5 wt. % acephate TG, 21.5 wt. % filler and 2 wt. % binding agent. Any other formulations between the formulations given can also be used. Granules with at least or about 80, 88, 89, 90, 91, 92, 93, 94, 95, 96, 97, and 98 weight % active ingredient (preferably acephate) are preferred in many cases. For example, to produce finished granules with a target of 90% active ingredient, the pre-mix would contain about 91.8% acephate TG (assuming 98% purity) and 8.2% inert filler and/or binding agent. The invented granules preferably do not have any other ingredients than those mentioned herein.

A preferred process to make the invented granules is as follows. The raw materials are received in bulk containers. The dry ingredients are pre-mixed and blended according to the formulation desired in a conventional paddle mixer or ribbon blender such as from Marion Mixers. The pre-mix of dry ingredients passes through a hammer mill, such as from Fitzpatrick Corp., in order to de-lump and provide a uniform mix. The dry pre-mix is then fed to a continuous flow agglomerator (preferably agglomerator 10, through inlet channel 30) at a pre-determined or metered rate and mixed with water to form granules. Water is preferably added such that the granules exiting the chamber 26 are about 3-6 wt. % water.

If desired, a binding agent may be added in liquid form along with water through liquid injectors 14. With reference to FIG. 1, the pre-mix is added through inlet channel 30, water and optionally other liquids are added through liquid injectors 14, the ingredients are turbulently combined and agglomerated into granules in chamber 26 via whirling blades 24 and drop out the bottom as agglomerated granules 28. Granules 28 preferably exit into a fluid bed dryer such as from Carrier Corp. where the granules are dried preferably to less than 1% moisture to form spheroidal agglomerates. As can be seen, granules 28 are not extruded.

Granules exiting the fluid bed dryer are screened to size; the over sized particles (which are retained on a screen size of about 6 or 8 or 10 mesh (U.S. Standard size)) are ground in a hammer mill and returned to the inlet of the screener. Fines, or under sized particles (which pass through a screen size of about 60 or 80 or 100 mesh (U.S. Standard size)) are recycled and blended into the virgin powder feed stream to be agglomerated. The process yields a dry flow, dust free, water soluble/dispersible granule having a diameter of preferably about 0.15-3.5, more preferably about 0.25-2.4, more preferably about 0.5-2, mm and a bulk density (loose) of preferably 29-37 or 30-36 or 31-35 or 32-34 or about 33, lbs/cubic foot and a bulk density (tapped) of preferably 32-40 or 33-39 or 34-38 or 35-37 or about 36, lbs/cubic foot.

The invented granules preferably are more porous and sponge-like than the hard, compacted extruded pellets produced according to U.S. Pat. Nos. 6,752,943, 6,875,381, 6,013,272, 6,337,323 and 6761897, such that the invented granules will disperse and dissolve faster in water. The invented granules preferably have a dissolution rate in water of about 9-15 or 10-14 or 11-13 or about 12, inversions (fill a 100 ml graduated cylinder with 100 ml of water, then add 1 g of sample and then stopper the cylinder, then invert the cylinder for the first inversion and permit the sample to settle to the bottom, then repeat these inversions until the sample has dissolved) and an attrition rate of about 0.01-5 or 0.01-3 or 0.01-2 or 0.1-1 or 0.2-0.9 or 0.3-0.8 or 0.4-0.7 or 0.5-0.6 or about 0.54, percent. Attrition is measured by obtaining 50 g of a sample which passes through a 10 mesh screen and is retained on a 40 mesh screen (−10+40), placing the 50 g sample in a Vanderkamp Friabilator for 100 revolutions, removing the sample and placing it on a 60 mesh screen, and calculating the percent that passes through the 60 mesh screen (−60). For example, if 0.4 g of the 50 g sample passes through the 60 mesh screen, the attrition rate is 0.8%.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A granule comprising, on a dry basis, at least 88 weight percent acephate, said granule being produced by a method comprising the steps of providing acephate in powder form along with a liquid to a noncompressive agglomerator and processing said powder and said liquid through said agglomerator to yield a granule, said agglomerator having a rotatable vertical shaft with a plurality of blades mounted to the shaft, wherein said granule has a diameter of 0.15-3.5 mm and a tapped bulk density of 32-40 lbs/cubic foot, said granule being less than 1% moisture and having a dissolution rate in water of not more than 15 inversions, said inversions being counted by filling a 100 mL graduated cylinder with 100 mL of water, adding 1 g of said granules, stoppering the cylinder, then inverting the cylinder for the first inversion and permitting the granules to settle to the bottom, then repeating these inversions until the granules have dissolved.

2. The granule of claim 1, said granule being, on a dry basis, at least 90 weight percent acephate.

3. The granule of claim 1, said granule being, on a dry basis, at least 95 weight percent acephate.

4. The granule of claim 1, said granule being, on a dry basis, 0.1-8 weight percent binding agent.

5. The granule of claim 1, wherein said liquid comprises water.

6. The granule of claim 1, wherein the blades are adjustable.

7. The granule of claim 4, wherein said binding agent is selected from the group consisting of starch, polyvinylpyrrolidone, vinyl pyrrolidone/vinyl acetate copolymer, and potassium sulfate.

8. The granule of claim 1, said granule being, on a dry basis, 1-15 weight percent filler.

9. The granule of claim 1, wherein said granule has a diameter of 0.25-2.4 mm.

10. The granule of claim 1, wherein said granule has a tapped bulk density of 33-39 lbs/cubic foot.

11. The granule of claim 1, said granule having a dissolution rate in water of not more than 14 inversions, said inversions being counted by filling a 100 mL graduated cylinder with 100 mL of water, adding 1 g of said granules, stoppering the cylinder, then inverting the cylinder for the first inversion and permitting the granules to settle to the bottom, then repeating these inversions until the granules have dissolved.

12. The granule of claim 1, wherein said agglomerator is a continuous agglomerator.

13. The granule of claim 1, wherein said agglomerator has a mixing chamber surrounded by a flexible sidewall which is continuously deformed during operation.

14. The granule of claim 1, wherein said granule has an attrition rate of about 0.01-5 percent.

15. The granule of claim 1, wherein, during processing, the vertical shaft rotates at a speed of 1000-3500 RPM.

16. The granule of claim 1, wherein said powder and said liquid is processed through said agglomerator in a retention time of less than 2 seconds.

17. The granule of claim 1, said granule being, on a dry basis, at least 97 weight percent acephate.

18. The granule of claim 1, said granule being, on a dry basis, at least 98 weight percent acephate.

19. The granule of claim 1, wherein said granule has a diameter of 0.5-2 mm.

20. The granule of claim 1, wherein said granule has a loose bulk density of 29-37 lbs/cubic foot.

* * * * *